(12) United States Patent
Andrade et al.

(10) Patent No.: US 6,501,549 B1
(45) Date of Patent: Dec. 31, 2002

(54) METHOD OF MEASURING CHEMICAL CONCENTRATION BASED ON SPATIAL SEPARATION AND RESOLUTION OF LUMINESCENCE

(75) Inventors: Joseph D. Andrade, Salt Lake City, UT (US); Chung-Yih Wang, Midvale, UT (US); Vladimir Hlady, Salt Lake City, UT (US); Philip M. Triolo, Salt Lake City, UT (US); Robert J. Scheer, Salt Lake City, UT (US)

(73) Assignee: University of Utah Research Foundation, Salt Lake City, UT (US)

( * ) Notice: Subject to any disclaimer, the term of this patent is extended or adjusted under 35 U.S.C. 154(b) by 0 days.

(21) Appl. No.: 09/077,694
(22) PCT Filed: Dec. 5, 1996
(86) PCT No.: PCT/US96/19472
  § 371 (c)(1),
  (2), (4) Date: Dec. 3, 1998
(87) PCT Pub. No.: WO97/20947
  PCT Pub. Date: Jun. 12, 1997

Related U.S. Application Data
(60) Provisional application No. 60/007,982, filed on Dec. 5, 1995.

(51) Int. Cl.$^7$ ............................ G01B 11/00; C12Q 1/66
(52) U.S. Cl. ...................... 356/388; 356/392; 356/394; 435/8
(58) Field of Search ................................ 356/344, 388, 356/392, 394; 436/172; 435/8, 4

(56) References Cited

U.S. PATENT DOCUMENTS

| 4,442,204 A | 4/1984 | Greenquist et al. |
| 5,089,424 A | 2/1992 | Khalil et al. |
| 5,736,410 A | * 4/1998 | Zarling et al. ............... 356/346 |

OTHER PUBLICATIONS

International Search Report—Mar. 26, 1997.

* cited by examiner

Primary Examiner—Frank G. Font
Assistant Examiner—Roy M. Punnoose
(74) Attorney, Agent, or Firm—TraskBritt

(57) ABSTRACT

A method and associated apparatus for measuring chemical concentration in a liquid sample based on spatial separation and resolution of light is disclosed. The method is preferably applied to sensitive, quantitative, luminescence-based biosensors which reads the analyte concentration via spatial distribution of the emitted light. The detection of light is used to assess the spatial position, rather than the intensity or wavelength, of emitted light. A bioluminescent or chemiluminescent reaction requiring, for example, ATP, NADPH or NADH as a specific, and sensitive co-factor is used. ATP or NADH concentration is modulated, "tuned," and/or regulated via, for example, an enzyme which consumes ("consumase") ATP, NADPH, or NADH, thereby producing a spatial distribution of ATP or NADH and a spatial distribution in the emitted light. By appropriate control of the consumase or "synthase" activity and kinetics, a sensitive, specific, and easily readable luminescent pattern is produced, permitting detection.

28 Claims, 10 Drawing Sheets

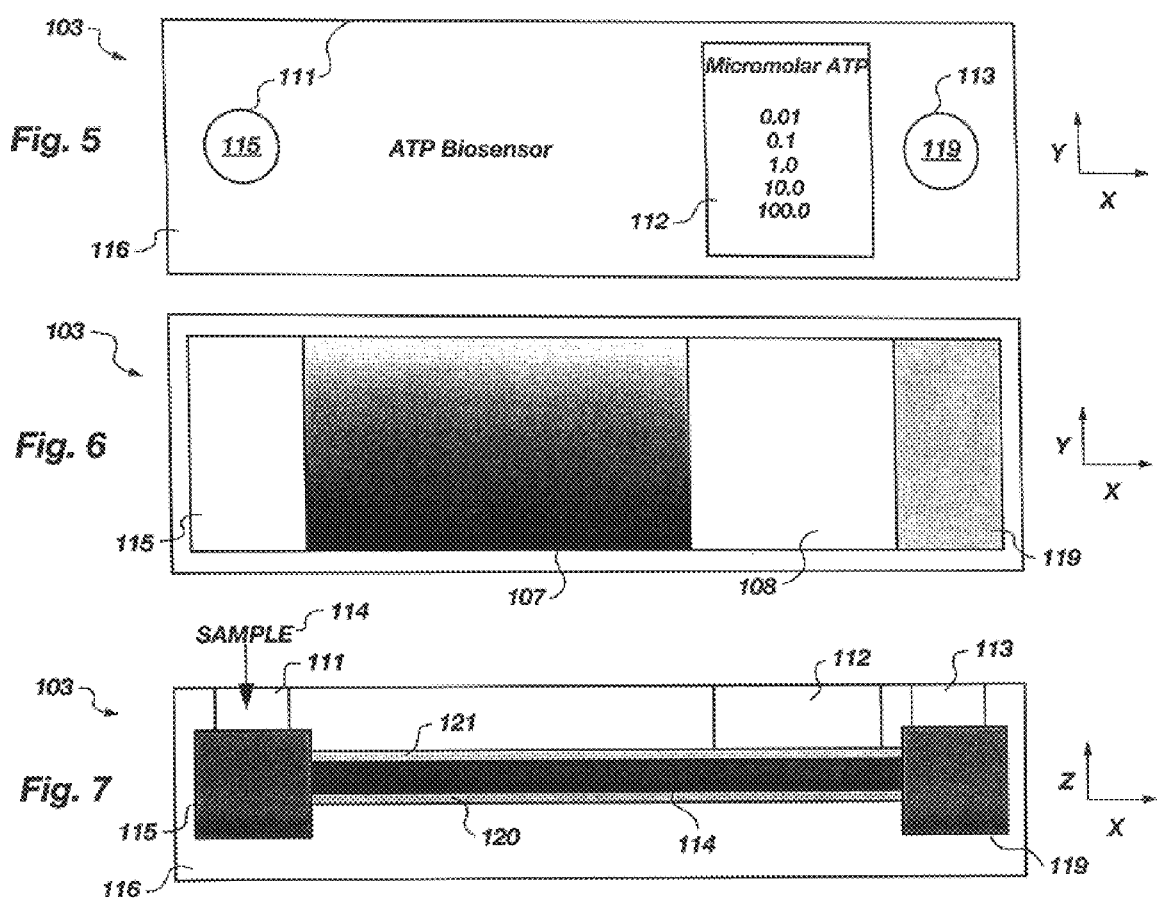

METHOD OF MEASURING CHEMICAL CONCENTRATION BASED ON SPATIAL SEPARATION AND RESOLUTION OF LUMINESCENCE

This application claims benefit of provisional application 60/007,982 filed Dec. 5, 1995.

TECHNICAL FIELD

The invention relates generally to diagnostic and detection devices, and specifically to such devices and associated methods which utilize an analyte-specific luminescent signal wherein the spatial position of the luminescent signal is related to the analyte concentration.

BACKGROUND

Bioluminescence is an enzyme dependent chemical oxidation process which results in photon emission. (1, 2). The photoproteins involved in such a process—for example, the luciferase series of oxidative enzymes—are now readily available in inexpensive form, produced by recombinant means. (3). Chemiluminescence is also a chemical oxidation process resulting in photon emission, generally without the need for enzymes. (4). Adenosine triphosphate ("ATP") and nicotinamide adenine dinucleotide ("NADH") are two molecules that play unique and central roles in biology. NADH is an ubiquitous electron donor as is the similar molecule NAD(P)H. ATP is generally recognized as one of the key energy currencies in bioenergetics. These two molecules act in a cyclic manner and can be regenerated or "recharged". (5). They are the basic coupling agents of cellular metabolism. Many biochemical enzyme processes involve one of these two molecules.

Evolution has produced bioluminescence processes based on these two molecules. Examples include firefly bioluminescence, wherein firefly luciferase acts on firefly luciferin in the presence of ATP and oxygen to produce an oxidized product which chemiluminesces with a very high efficiency, and bacterial bioluminescence, wherein bacterial luciferase and an oxidoreductase, in the presence of alkyl aldehydes such as decanal, together with NADH and oxygen, produces an excited-state product which chemiluminesces. Both reactions require the presence of oxygen, although the particular luciferases and luciferins involved differ.

Literature exists describing the development of biosensors for ATP and ATP-dependent processes and for NADH and NADH-dependent processes, using the firefly and bacterial luciferase enzymes, respectively. Such biosensors generally involve fiberoptic or other waveguided means of delivering the luminescence to a sensitive device such as a photo-multiplier tube which can accurately measure light intensities. (6–9). Although one of the most portable and most sensitive photon detectors available is the human eye, it cannot be relied upon to accurately measure even relative light intensity. (10).

Luciferases have also been used as labels for a wide range of clinical diagnostic chemical tests. Since the firefly luciferase reaction is dependent on an ATP co-factor, it has been extensively used in the development of biosensors for the measurement of ATP, including detection of bacteria and other microorganisms based on the release of intracellular ATP. Instrument-based commercial biosensor kits for ATP quantification can currently attain a detection threshold of about $10^{-13}$ grams of ATP. (11). Likewise, bacterial luciferase which utilizes NADH, a ubiquitous chemical in bioenergetic pathways, has also been widely used for biosensing applications. Such applications have, however, been frustrated by the relative instability of these enzymes and the difficulty of incorporating them into practical and reliable biosensors.

Numerous enzymes exist which are linked to ATP consumption or ATP production, most of which are specific to another chemical substrate, for example, glycerol, glucose, etc. These "front end" enzymes, coupled to a basic ATP detection device approach using luciferase and luciferin, permit the development of individual sensors or sensor channels for each of those substrates or analytes. (7–9, 12, 13). Analogous analytical systems exist for bacterial luciferase. (7,8).

DISCLOSURE OF THE INVENTION

The invention includes analytical chemistry systems, specific for particular analytes, including enzymes, which are specific, quantitative, rapid, direct-reading (via luminescence), sensitive, have a long shelf-life, are stable, disposable, and relatively inexpensive. The entire analytical instrument may be built into the sampling device to produce an analytical chemistry device that does not require separate instrumentation. Both analyte detection and readout utilize light produced by bioluminescence or chemiluminescence. Specificity is provided by the incorporation of specific enzymes into the device. The invention is particularly useful for the direct analysis of ATP using firefly luciferase coupled with other enzyme-mediated biochemical processes which either produce or consume ATP. As used herein, a "consumase" is an enzyme which consumes the ATP, NADPH, or NADH. A "synthase" is an enzyme which produces ATP or NADH. However, other analytes can be linked to the ATP reaction. In a similar fashion, the invention is also applicable to analysis of analytes linked to reactions involving NADH and NAD(P)H.

A sensor according to the invention generates an analyte-specific luminescent signal in a specific spatial position that can be read by a user. It is specifically configured to produce light in a particular area of a two- or three-dimensional device, although one-dimensional geometries can be used (e.g. capillaries, rods, waveguides, etc.). It is the spatial position of the light on (or in) the device, rather than its intensity, which is related to the concentration of analyte or substrate. The human eye is much more capable of directly detecting the spatial position of a light source in a reproducible and quantitative manner, than it is of detecting changes in light intensity.

The invention produces a spatial distribution of the emitted light where such spatial distribution is proportional to the analyte concentration. The human eye or other means for light detection, e.g. chemical means such as photographic film or electronic means such as a charge coupled device ("CCD"), is used primarily to assess spatial position rather than absolute light intensity. This is achieved by carefully controlling the luciferase concentration and by modulating, tuning, and "filtering" the ATP or NADH concentration such as through the use of a second ATP or NADH consuming enzyme. This ATP or NADH "consumase" is selected to have a rapid turn over, and to serve as an ATP or NADH concentration regulator or "filter". The consumase is deposited in different spatial regions of the one-, two- or three-dimensional sensor at different concentrations.

According to the invention, a device for the quantitative analysis of one or more chemicals employs a spatial distribution of luminescence, and includes (a) a mixture of two or more chemicals that combine to produce luminescence, (b) a "chemical filter" or gradient that produces a spatially distributed precursor component of the mixture which results in a spatial distribution of luminescent signal, and (c) means for containing the chemicals in various spatial relationships to facilitate chemical reactions and luminescent signal detection.

The invention has industrial applicability in the areas of biology, biochemistry, biophysics, medicine, health, sports, environment, education, food, dairy, brewery, research, chemical, and related areas with chemical monitoring and analysis needs.

BRIEF DESCRIPTION OF THE FIGURES

FIG. 5 graphically depicts a top view of an ATP sensor according to the invention.

FIG. 6 graphically depicts a cut-away top view of the ATP sensor of the preceding figure.

FIG. 7 graphically depicts a cut-away side view of the ATP sensor of the preceding two figures.

BEST MODE OF THE INVENTION

The sensor is designed to produce light in a particular area of a one-, two- or three-dimensional sample. With the sensor, it is the spatial position of the light, rather than its intensity, which is related to analyte concentration. The human eye or other spatial detector can then be used to detect the spatial position of the light in a reproducible and quantitative manner. The sensors utilize a stable mixture of chemicals which combine to produce luminescence (e.g. luciferase and luciferin) integrated into a hydrophilic matrix (or matrices) integrated with, coupled to, or otherwise associated with a sample distribution system.

Figure 1:
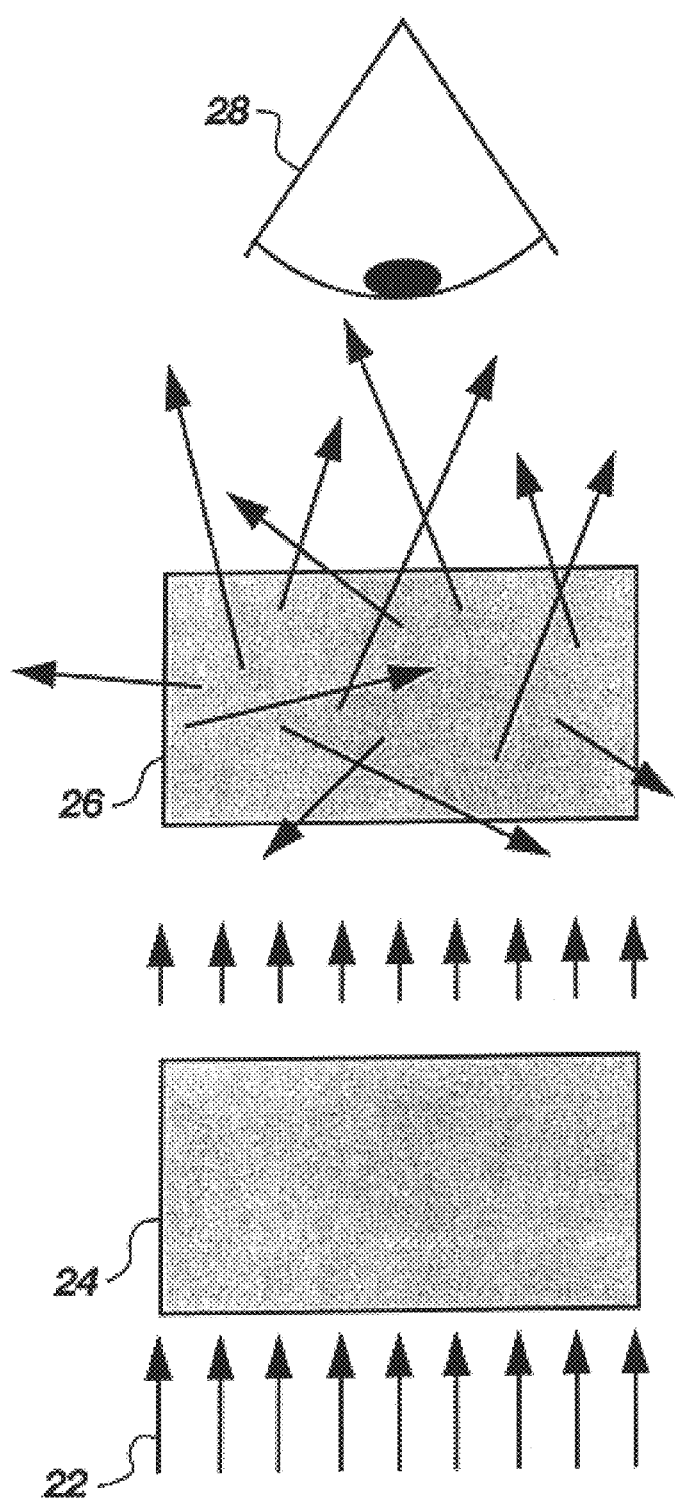
FIG. 1 graphically depicts a single channel ATP sensor.

FIG. 1 graphically depicts a single channel ATP sensor, generally 20, where the ATP consumase is immobilized in (or on) a hydrophilic gel matrix 24. The consumase, such as apyrase, converts some of the analyte ATP to ADP thus limiting or modulating the amount of ATP reaching a transduction region 26 containing chemicals which combine with ATP to produce luminescence (e.g. a luciferase and luciferin). In FIG. 1, a specific ATP sample 22 is contacted with the ATP consumase immobilized in an hydrophilic agarose gel matrix 24. The sample 22 is uniformly distributed, and diffuses into the ATP consumase-gel layer 24, at which time, the ATP is partially consumed by the consumase via conversion to adenosine diphosphate ("ADP") and adenosine monophosphate ("AMP"). A lower concentration of ATP thus enters the transduction region 26 (e.g. a second hydrophilic gel layer such as an agarose gel matrix), which contains an optimum concentration of luciferin and luciferase in, for example, the gel matrix. As the ATP interacts with the, for example, luciferase and luciferin, photons are emitted which are then detected by the operator 28, or other means of light detection, positioned preferably at the top of the sensor.

Figure 15:
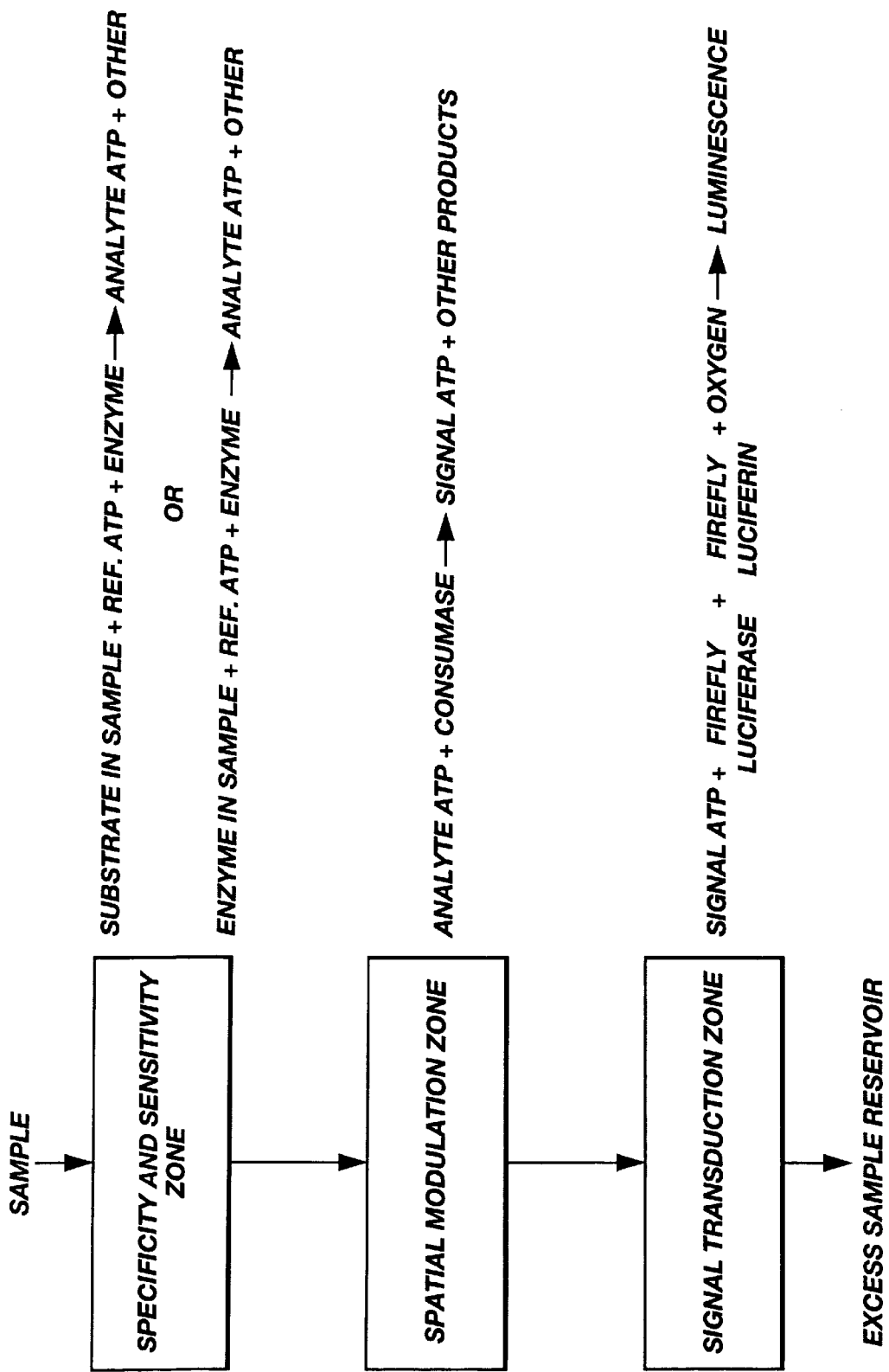
FIG. 15 is a flow diagram depicting a method according to the invention.

As best shown in FIG. 15, the invention can, in one aspect, be conceptually divided into three or more "zones". As depicted in FIG. 15, a liquid sample 96 is placed in (or in fluid communication with) a Specificity and Sensitivity Zone 150. In this zone, the substrate to be analyzed (or, conversely, enzyme to be analyzed) in the sample is reacted with Reference ATP and corresponding enzyme (or, conversely, corresponding substrate). This reaction results in Analyte ATP. The Analyte ATP passes through to the Spatial Modulation Zone 152 in fluid communication with zone 150 where it reacts with consumase to form Signal ATP and by-products. The Signal ATP then passes to a Signal Transduction Zone 154 (which is in direct or indirect fluid communication with the Spatial Modulation Zone 152) which zone 154 includes a luciferase (or luciferases) and a luciferin (or luciferins). The Signal ATP, luciferase, and luciferin react with oxygen to produce luminescence. Optionally, an Excess Sample Reservoir 156 can be in fluid communication with one or more of the zones to control sample volume and to collect excess sample.

The same general approach illustrated in FIG. 15 may be used with NAD$^+$ being substituted for ATP and bacterial luciferase replaces firefly luciferase in the transduction zone.

In fact, many possible enzyme-substrate reactions exist linked to either ATP, NADH or NAD(P)H which can be used with the invention. This makes possible the quantitative measurement of saccharides, amino acids, vitamins, ketones, alcohols, and hormones. For example, the following list of enzymes (18) (with enzyme classification number following the enzyme identification in parenthesis), substrates, co-reactants, and reaction products provides just a few of the possible configurations for a sensor according to the invention:

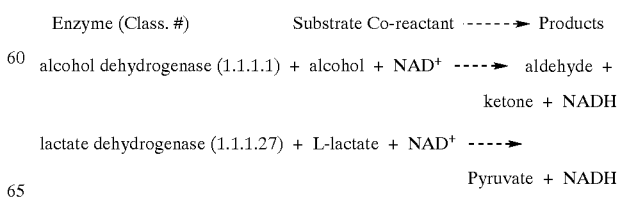

-continued biliverdin reductase (1.3.1.24) + bilirubin + $NADP^+$ ----▶ biliverdin + NADPH alanine-dehydrogenase (1.4.1.1) + L-alanine + $NAD^+$ ----▶ pyruvate + $NH_3$ + NADH hexokinase (2.7.1.1) + D-hexose + ATP ----▶ D-hexose-6-phosphate + ADP ammonia kinase (2.7.3.8) + ammonia + ATP ----▶ phosphoramide + ADP creatine kinase (2.7.3.2) + creatine + ATP ----▶ phosphocreatine + ADP The previously-identified creatine reaction is an example of one step in an "enzyme cascade" reaction which can be used with the invention for analyte analysis in that it may be preceded by the following reaction for the purpose of analyzing creatinine in urine:

creatininase (3.5.2.10)+creatinine --->creatine

In a similar fashion, it is possible to employ enzyme reactions which produce peroxide (e.g. $H_2O_2$) that can be directly detected by reaction with the chemiluminescent precursor reagent, luminol, which reacts with the aid of a catalyst or co-reactant. An enzyme gradient may be used to produce a peroxide gradient which then "feeds" the luminol in the transduction zone. Esters of oxalic acid and other chemiluminescent precursors sensitive to hydrogen peroxide may also be employed. For example, reactions which could be incorporated into the spatial modulation zone include:

Glucose+$O_2$+glucose oxidase--->glucono-lactone+$H_2O_2$ and

Cholesterol+$O_2$+cholesterol oxidase--->cholesterone+$H_2O_2$

The corresponding transduction zone reaction for the peroxide would be:

Luminol+$H_2O_2$+catalysts (or co-reactants)--->luminescence+by-products

Similar to the creatine situation, multi-enzyme cascade systems may also be used with the invention to generate a peroxide product when no single enzyme could be used.

Furthermore, besides apyrase, other consumases which may be used with the invention include other ATP-ases such as various kinases e.g., Hexokinase.

Furthermore, the activity of any of the enzymes described herein can be "amplified" or enhanced to facilitate the generation of luminescent signal with agents such as flavin reductase, albumin, coenzyme A, surfactants, or mixtures thereof. Also, the ATP or NADH, or NADPH (dihydronicotinamide adenine dinucleotide phosphate) concentration may be enhanced in the sensors of the invention.

Figure 2:
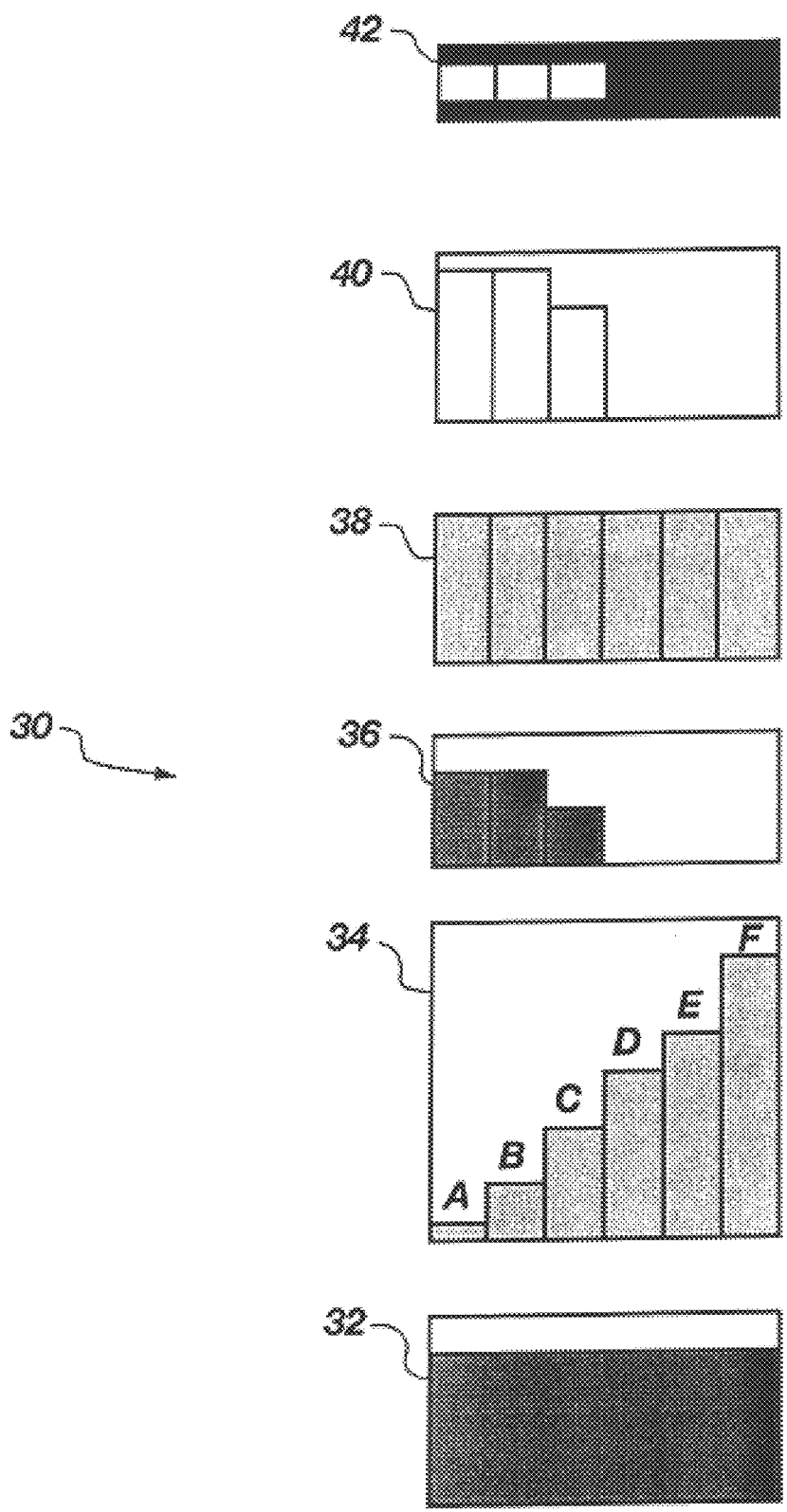
FIG. 2 graphically depicts a multi-channel ATP detector according to the invention.

FIG. 2 depicts a multi-channel ATP sensing device according to the invention, generally 30. The device 30 accepts a uniform ATP analyte concentration 32, a matrix 34 of six discrete channels (A, B, C, D, E, F), each having a sequentially increasing or decreasing consumase concentration (thus creating a gradient in the device), leaving residual ATP in some fraction of the six channels 36. For a uniform input of ATP into the consumase gel channels, each channel delivers a different ATP concentration to a luciferase/luciferin layer 38. The luciferase/luciferin layer 38 may be luciferin and luciferase uniformly distributed in an agarose-gel matrix. Alternatively, the luciferin and luciferase distribution in 38 may be designed or selected to be nonuniform. Depending on the specific consumase concentrations, the luciferase/luciferin concentrations, and the concentration of ATP, the light output will be at a maximum at a position corresponding to a minimum consumase concentration, and will be at a minimum at a position corresponding to a maximum consumase concentration.

By appropriate selection of the concentration ratios, and by appropriate selection of a consumase (or consumases) with the appropriate turnover rate (matched to the delivery of ATP into the consumase-containing gel), a specific spatial illumination pattern is obtained. The resultant output light intensity 40 for each of the channels creates a spatial illumination pattern 42 that can then be detected visually, photographically, or electronically.

Figure 3:
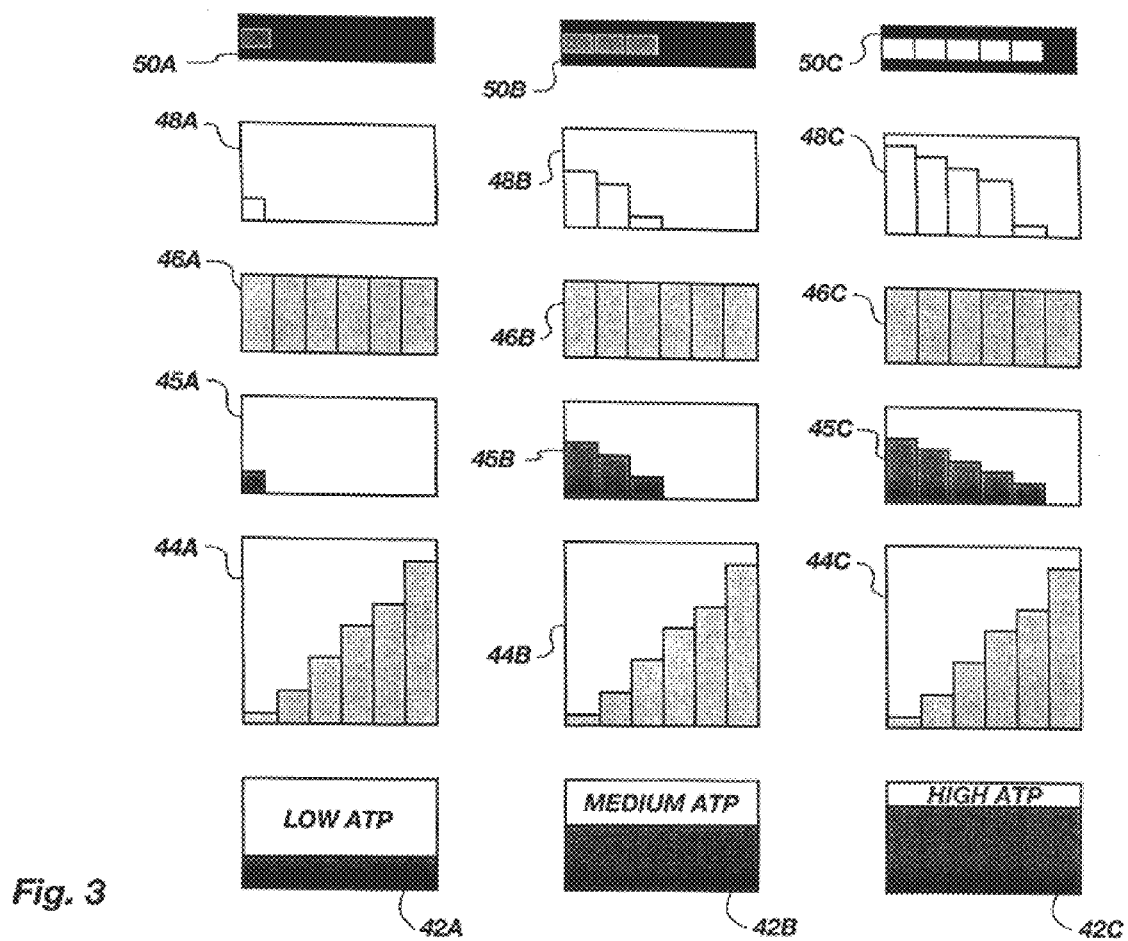
FIG. 3 graphically depicts three ATP detectors arranged according to the invention.

FIG. 3 graphically depicts three different ATP-containing samples exposed to three identical and discrete multi-channel ATP biosensors 42A, 42B, 42C each having six step-gradient consumase channels 44A, 44B, 44C, and constant uniform luciferin and luciferase concentrations 46A, 46B, 46C. ATP is schematically shown being delivered to the consumase gel layers 44A, 44B, 44C, containing six channels of different consumase concentration. Such a "gradient" arrangement results in a change in the ATP concentration delivered to the luciferase-luciferin gel 45A, 45B, 45C. There is a resultant increase in the light intensity (photon output intensity 48A, 48B, 48C for each channel) as a function of increased ATP. Also, the resulting spatial position or spatial distribution of light 50A, 50B, 50C for each of the three biosensors changes as a function of ATP concentration, with the spatial distribution for the high concentration ATP 50C depicting a longer line of luminescence than the spatial distribution for the low ATP 50A or medium ATP 50B, i.e., a spatial position is directly correlated with the ATP level in the liquid sample. Spatial position can be determined or measured by an operator viewing the device without special instruments and without great concern for dark adaptation or specific intensity values.

Besides the herein described concentration gradients, other gradients affecting the rate of consumption of the substrate can be used. For example, different enzymes having different catalytic rates can be used, or the same concentration of the same enzyme can be used throughout the material, but portions of the material are selectively reacted with increasing amounts of enzyme antagonist (or agonist) to form a de facto gradient, or a thermal gradient could be used where the same concentration of the same enzyme is used, but the temperature in a particular area of the gradient is optimized, while the other areas of the "gradient" are not optimized, or the temperatures are appropriately gradated, or the amount or type of co-factor is manipulated to create a gradient. Also, the same concentration of one or more enzymes or substrates could be used but there could be a spatial variation or distribution chosen which would perform a similar role as a chemical concentration gradient.

The sensors generally contain reference channels. For example, when performing urinalyses, creatinine might be determined as a means to standardize test samples.

In an alternative embodiment, the discrete, parallel multi-channel device described in FIG. 3 can be replaced by a device having a continuous or semi-continuous gradient of consumase distributed in one, two, or three dimensions. Such an arrangement is illustrated in FIG. 4.

Figure 4:
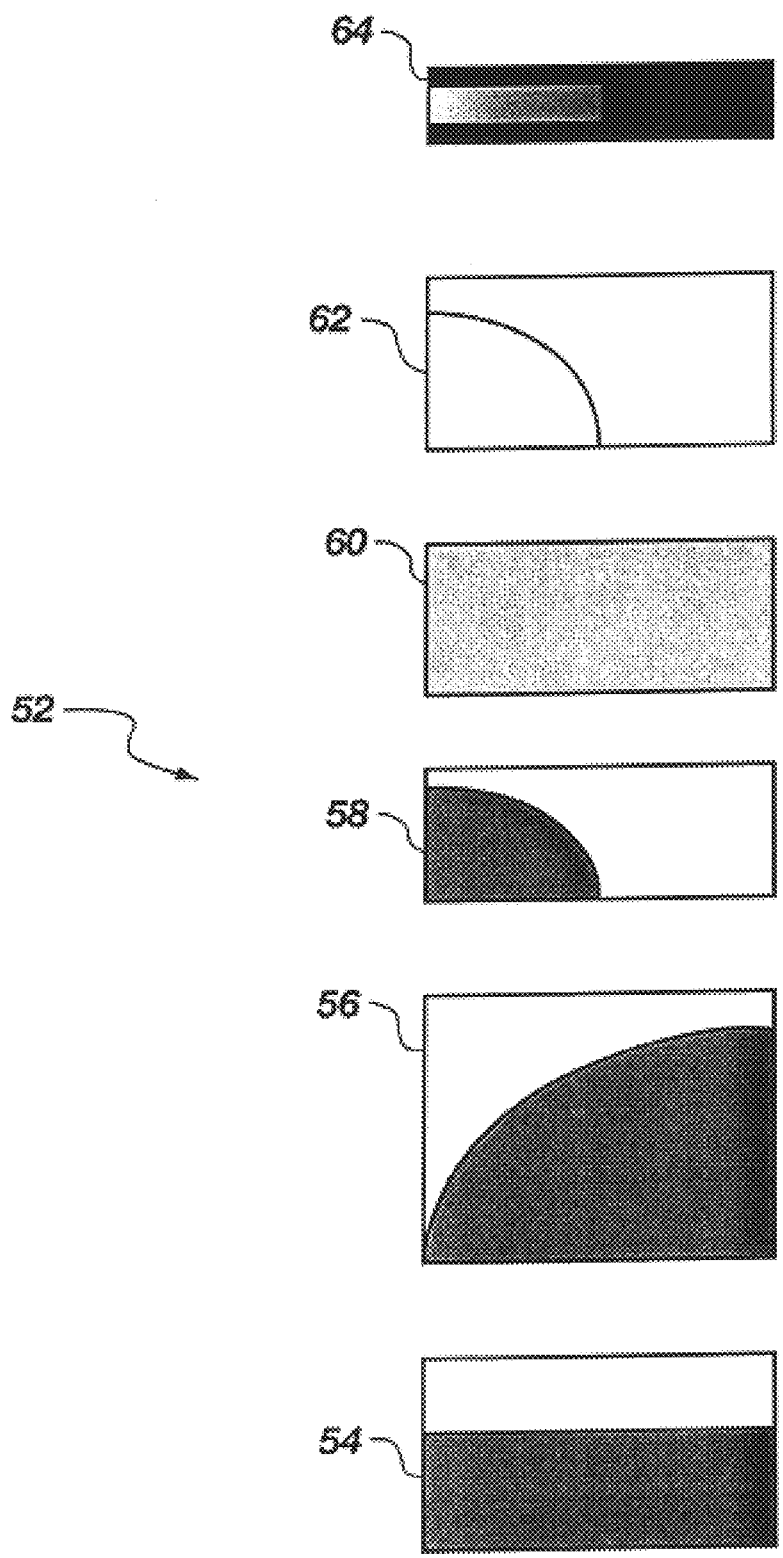
FIG. 4 graphically depicts a single channel ATP detector according to the invention, wherein a single channel having a consumase gradient in one or more dimensions modulates the amount of ATP reaching the transduction layer containing luciferin and luciferase.

FIG. 4 depicts an ATP detector, generally 52, having a single channel with a spatially continuous consumase gradient 56 in one or more dimensions which modulates the amount of analyte ATP 54 reaching the transduction layer 60 containing a uniform distribution of luciferin and luciferase in a hydrophilic gel matrix. The consumase gradient 56 converts a proportional amount of the analyte ATP into ADP. The remaining ATP 58 is then delivered to the transduction region 60 containing a uniform luciferin-luciferase distribution in a hydrophilic gel matrix. The photon output intensity distribution 62 creates a spatial illumination pattern 64 which indicates the actual concentration of ATP analyte 54 in the sample. The actual ATP concentration is determined by visually observing where the light on the sensor ends and comparing that position to a pre-calibrated scale on the sensor.

In the device of FIG. 4, a uniform analyte ATP concentration is delivered to a spatially continuous consumase modulation region. The consumase is supported in (or on) a hydrophilic matrix. In turn, the matrix, for example a gel, may be supported on a fibrous or porous network. The distribution of the consumase is fashioned in a well-defined spatial or concentration gradient configured to produce a well-defined spatial distribution of analyte ATP and subsequently of light at the output end of the sensor. As the analyte ATP moves into the consumase region, it is, in part, converted to ADP with the residual ATP moving on towards the luciferase-luciferin transduction region which is also supported in (or on) a hydrophilic matrix. The residual ATP, which is now spatially asymmetric, chemically reacts with the spatially uniform distribution of luciferase and luciferin in the presence of oxygen to produce luminescence. The light so produced has a spatial distribution which matches the residual ATP distribution and which is, in turn, proportional to the concentration of the original ATP concentration and the consumase gradient. As with the discrete, discontinuous consumase gradient biosensor shown in FIG. 3, the continuous consumase gradient biosensor has a spatial light output which can be directly correlated with the analyte ATP level, where the spatial distribution of light can be visually, photographically, or electronically detected. Such a light distribution can be viewed by an operator without special instruments and without great concern for dark adaptation or specific intensity values.

In one embodiment, an ATP-specific sensor platform employs the spatial distribution of light for quantification of ATP. Such a device may be employed for microorganism-derived ATP analyte analysis where the concentration of ATP so determined is directly related to the number of microorganisms. Microorganisms may be eukaryotic cells, such as those derived from higher plants and animals or prokaryotic cells, such as bacteria. Bacterial cell membranes can be disrupted with specific chemicals such as ethanol, or with detergents or with enzymes or combinations of chemicals, enzymes and detergents. Such treatment effectively releases the intracellular contents, including the ATP to be analyzed. (11).

FIGS. 5, 6 & 7 depict three different views of an ATP biosensor, generally 103. An ATP analyte-containing sample is added at sample port 111. A first, reading window 112 allows a user to see the actual concentration of analyte ATP. The effective ATP analysis range of the sensor may be indicated in adjacent window 112 (e.g. 0.01 to 100 micromolar). Other concentration ranges are possible as well. A second window 113 serves to indicate that the sample successfully traveled the full length of the biosensor 103, and activated both the consumase-modulation and luciferin-luciferase transduction regions. The biosensor housing 116 may be any suitable fabricated material.

A sample 114 containing ATP is added at the sample port 111. The liquid sample rapidly wets a porous or fibrous hydrophilic material 115 which serves as a sample reservoir. Suitable materials for this use include natural or synthetic materials, such as bonded cellulose acetate TRANSORB wick (e.g. American Filtrona R17381). The sample then migrates from the reservoir 115 through a sample analysis region 114 by capillarity. This region 114 includes a sample modulation region 107 and a signal transduction region 108 (FIG. 6). The liquid then flows into an excess sample reservoir 119. The absorbent material used in sample reservoir 119 can be the same material that is used in the filling reservoir 115. Reservoir 119 serves to pull adequate sample through the analysis region 114. This material also serves as a support for a water-based dye which changes its appearance when it is dry to a visible color or other distinctive appearance when it becomes wet, thus indicating that aqueous sample has successfully traversed the entire analysis region.

The sample analysis region 114 is made of a wicking material such as cellulose fibers or a porous material such as open cell, hydrophilic polyurethane sponge which serves as a support for a hydrophilic polymer which is, preferably, a low-gelling, temperature agarose such as seaprep or seaplaque (FMC Corp.). The sample analysis region 114 is partitioned into two spatially distinct regions—the analyte modulation region 107 and the signal transduction region 108 (FIGS. 6 & 7). In the modulation region 107, the sample-containing ATP contacts the agarose-coated cellulose fibers which have a spatially variable concentration of a consumase (e.g. an ATP-ase such as apyrase). Apyrase is commercially available from Sigma Chemical Co., and may be incorporated into the agarose coating on the cellulose fibers. The consumase consumes some of the ATP by converting it into ADP. The remaining ATP (which is now spatially distributed along the "Y" axis) is carried along in the "X" direction by capillary action into the transduction region 108 which contains a spatially uniform concentration of luciferase and luciferin, both of which are supported by the agarose gel on cellulose fibers. The luciferin is available from Sigma Chemical Co. and luciferase (purified firefly luciferase) may be obtained from Molecular Probes, Inc. or produced by genetic engineering techniques. (3).

As the analyte ATP enters the transduction region 108, it interacts with luciferin, luciferase and oxygen to produce light which is detected. The chemiluminescent light is visible as a glowing numerical indicator viewed through window 112 with the actual concentration read as the largest number illuminated on the visible scale.

In an alternative embodiment (not shown), a waveguide, lens, or other light transmission means is used to direct, enhance or focus the light for better viewing by the observer. Further, the light produced by the device may be amplified, multiplied, wavelength shifted, or otherwise altered to enhance the observer's determination of its position.

The analysis region 114 is contained in the vertical ("Z") dimension by, for example, transparent polymeric films 120, 121 which run between the two reservoirs 115, 116 and sandwich the analysis region 114. Alternatively, two glass or similar inert material plates could be used. Such polymeric films may be made of various polymers, but polyester provided by PMC Corp. is quite suitable.

The depicted biosensor can be made relatively small, having dimensions of several centimeters in the "X" and "Y" dimensions, and several millimeters in the "Z" dimension. Because of the susceptibility of luciferase and luciferin to degrade in the presence of oxygen or moisture, the agarose gel in the sensor is preferably dehydrated prior to final assembly. Various disaccharides such as sucrose and/or trehalose may be added to enhance the structural stability and thus the activity of the macromolecules. The entire device may also be stored in a metal foil package, and backfilled with an inert gas such as argon or nitrogen or partially evacuated for long-term storage stability.

Figures 8, 9:
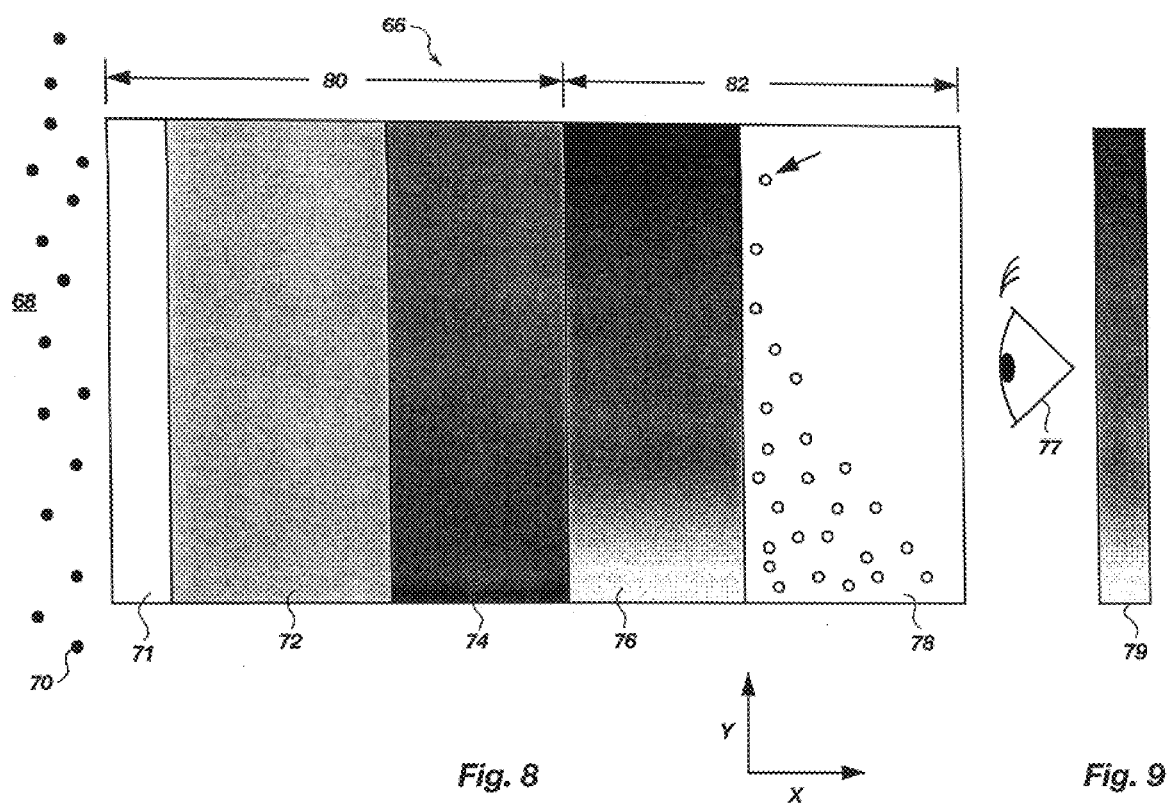
FIG. 8 graphically depicts a top view of a generic carbohydrate sensor based on the partial consumption of ATP which in turn is modulated by a consumase gradient and converted to light in the transduction region by luciferase and luciferin.
FIG. 9 graphically depicts a side view of the sensor of the preceding figure.

FIG. 8 depicts a generic carbohydrate (e.g. saccharide) sensor, generally 66. The depicted sensor 66 has a sample containing portion 68, which contains the saccharide analyte 70, a portion 71 containing a pH adjustment region, a portion 72 containing ATP in a matrix, a portion 74 containing a kinase in a matrix, a portion 76 containing a consumase (e.g. apyrase) gradient, and a portion 78 containing luciferin and luciferase. The various component containing portions are, sequentially, in fluid communication with one another. For example, the sample-containing portion 68 is in fluid communication with the ATP-containing portion 72, which is also in fluid communication with the kinase-containing matrix 74. The kinase-containing matrix 74 also communicates with the gradated consumase-containing portion 76, which itself is in fluid communication with the luciferin-luciferase-containing portion 78.

Conceptually, the sensor 66 can be split into a sensor front portion 80 comprising the ATP-containing region 72 and kinase-containing region 74, and an ATP sensor platform end 82 comprising the consumase containing region 76 and luciferin and luciferase-containing region 78. This sensor 66 is based on the partial consumption of ATP which in turn is modulated by a consumase gradient and converted to light in the transduction region 78 by luciferase and luciferin. The resultant signal photons are spatially distributed 79 to yield an indication of original saccharide concentration.

FIG. 8 shows the sensor contacting an aqueous sample 68 containing a saccharide analyte. The water and analyte (e.g. a saccharide) are drawn into the pH-adjustment region 71, the ATP-containing region 72, and the specific kinase-containing region 74. The saccharide is phosphorylated, and ADP is produced, thus depleting the ATP concentration. The remaining ATP, called "analyte ATP", is then drawn into a consumase region 76 where there is a uniform, well-defined concentration gradient of the consumase. Analyte ATP is partially converted to ADP by the consumase leaving a residual amount of "signal ATP" which is spatially distributed. This signal ATP is then transported into a region of uniform luciferin and luciferase 78 immobilized in or on a matrix. The luciferase catalyzes the reaction of signal ATP with luciferin to produce a spatial distribution of light 79 which can then be directly visually correlated 77 with the amount of signal ATP and, in turn, analyte ATP, and thus the saccharide concentration in the original sample. The spatial distribution of the light 79 is depicted in FIGS. 8 & 9, and the reactions summarized as follows:

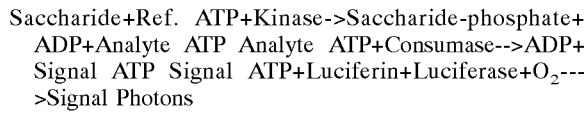

Saccharide+Ref. ATP+Kinase->Saccharide-phosphate+ ADP+Analyte ATP Analyte ATP+Consumase-->ADP+ Signal ATP Signal ATP+Luciferin+Luciferase+$O_2$--->Signal Photons In an alternative embodiment, the previously-described "back-end" ATP-specific sensor platform is coupled to a front end sensor having specificity for any of the many saccharides (e.g. glucose, fructose, galactose, and lactose), alcohols, aminoacids, ketones, vitamins, hormones, etc. which are biochemically linked to ATP, NADH and NAD (P)H. The spatial distribution of light is again employed for the quantification of the analyte of interest.

Figure 10:
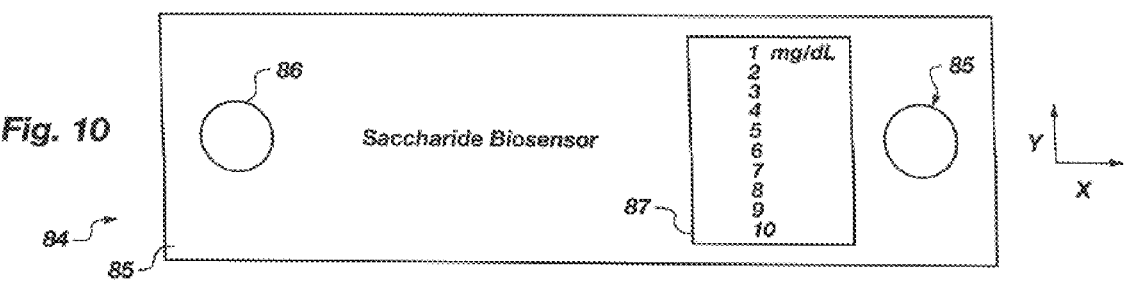
FIG. 10 graphically depicts a top view of a saccharide biosensor according to the invention.
Figure 11:
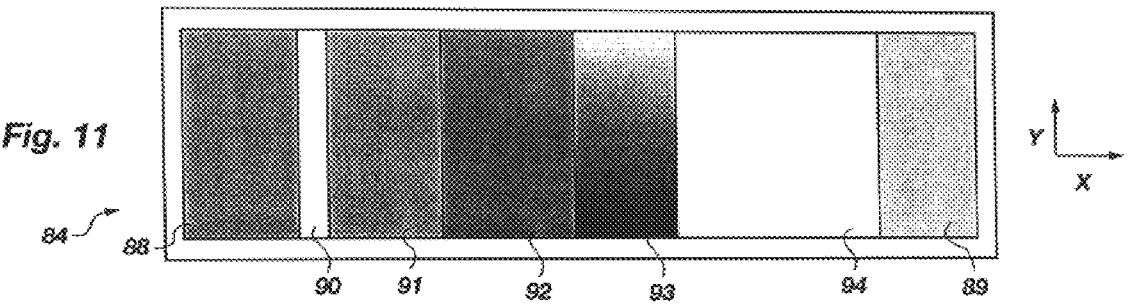
FIG. 11 graphically depicts a cut-away top view of a sensor of the preceding figure.
Figure 12:
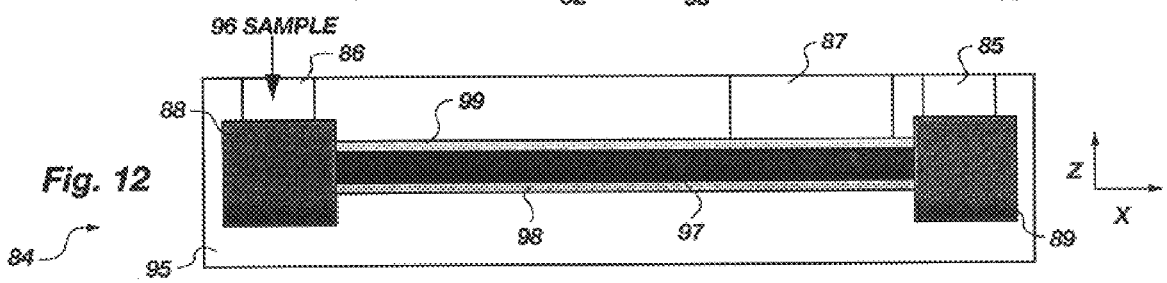
FIG. 12 graphically depicts a cut-away side view of the sensor of the preceding two figures.

FIGS. 10–12 depict various views of one biosensor, generally 84, according to the invention. Actual sample analyte 96 is added at sample port 86. Reading window 87 is where the actual concentration of analyte in sample is indicated. In the depicted embodiment, the level of saccharide is indicated as a range of from one to ten milligrams per deciliter. Other ranges are, of course, possible. A window 85 serves to indicate that the sample successfully traveled the full length of the biosensor 84, and interacted with the various regions of the sensor. The biosensor housing 95 may be any suitably fabricated material. A sample 96 containing the analyte carbohydrate is added to the sample entry port 86. The aqueous sample rapidly wets a porous or fibrous hydrophilic material 88 which serves as a sample reservoir. Suitable materials for such use include natural or synthetic polymers.

The sample is then transported from the reservoir 88 through the sample analysis region 97 by capillary action. This region contains sample conditioning and modulating regions and a signal transduction region 94. The sample then flows into the excess sample reservoir 89. The material in sample reservoir 89 can be the same material as that filling reservoir 88. Reservoir 89 serves to pull adequate sample through the analysis region 97. This material also serves as a support for a water-based chemical or dye which changes appearance upon interaction with the sample.

The sample analysis region 97 is comprised of a wicking material such as cellulose fiber or a porous material such as hydrophilic polyurethane sponge which serves as a support for a hydrophilic polymeric material, preferably a low-gelling temperature agarose (FMC Corp.). The sample analysis region 97 is partitioned into a number of spatially distinct regions as best shown in FIG. 11. There is a pH adjustment region 90 (e.g. a buffering region) and a reference ATP region 91. There is also is an adjacent kinase region 92. It also includes an analyte-modulation region 93 and a signal transduction region 94. In the modulation region 93, the sample containing analyte AIP contacts the agarose-coated cellulose fibers which have a spatially variable concentration of consumase. The consumase (e.g. apyrase) is associated with (e.g. supported on or incorporated into) the agarose coating on the cellulose fibers.

The material comprising the analysis region 97 is bounded in the vertical ("Z") dimension by generally parallel transparent members 98, 99. These members may be polymeric films (e.g. polyester), glass, or other inert substance.

The consumase consumes some of the ATP by converting it into ADP. The remaining ATP—which is now spatially distributed in the "Y"dimension (FIGS. 10 & 11) is carried along in the "X" direction by capillary action into the transduction region 94 which contains a spatially uniform concentration of luciferin and luciferase, both of which are supported by the agarose gel on the cellulose fibers.

As the signal ATP enters the transduction region 94, it interacts with the luciferin, luciferase and oxygen to produce light which is visible to the naked eye in the dark. The chemiluminescent light is visible as a glowing numerical value which can be viewed through window 87 with the actual concentration being read as the largest number illuminated on the visible scale.

The resulting biosensor 84 can be relatively small, having dimensions of several centimeters in width and length, and several millimeters in thickness.

Figure 13:
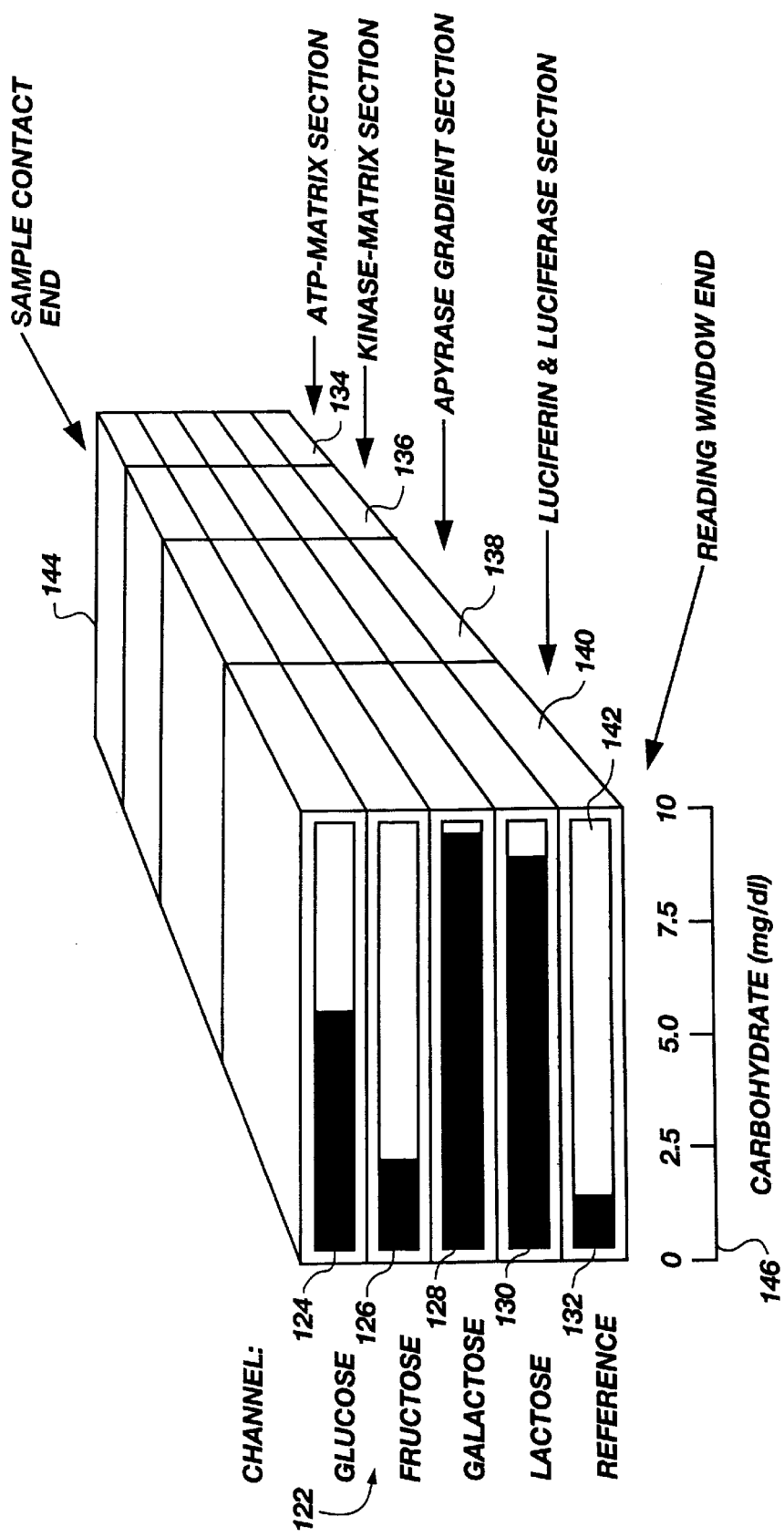
FIG. 13 graphically depicts a four channel carbohydrate biosensor with a fifth reference channel.

FIG. 13 depicts a four channel carbohydrate sensor that utilizes a fifth reference channel. The depicted sensor, generally 122, has five separate carbohydrate sensor units 124, 126, 128, 130, 132, not unlike the sensor units of FIGS. 10–12, stacked upon one another to form a single sensor 122. Each such separate sensor unit has, positioned adjacent and in fluid communication with one another, an ATP-matrix section 134, a kinase matrix section 136, a consumase gradient section 138, a luciferin-luciferase section 140, and thereafter reading windows 142. The reading window may have a lens or light transmission device to aid the observer in viewing the light produced in the luciferin-luciferase section 140 and displayed in the reading window end 142.

In the depicted embodiment, the top most sensor unit 124 is configured to determine the concentration of glucose (e.g. in milligrams per deciliter) in a liquid sample which is applied to a sample contact end 144. A reference concentration scale 146 for reading the concentration is provided, preferably associated with the sensor's housing for easy reading by an observer. The next lower sensor unit 126 is configured to determine the concentration of fructose. The next lower sensor unit 128 is configured to determine the concentration of galactose. The next lower sensor unit 130 is configured to determine the concentration of lactose. The bottommost sensor unit 132 is a reference standard, used to ensure that the device is operating properly.

In one embodiment (not shown), the channels are also stacked, but more as a laminate so as to expose several windows on the top surface and simultaneously on a single plane of the sensor.

A number of other variables in the analysis and optimization include the actual sample size to be delivered, the rate of wicking, the diffusion of the appropriate substrates into the two gels, and the specific time or times when the luminescence should be observed by the user. It should also be noted that several zones or domains may be integrated together. For example, the reference ATP zone may possibly be superimposed or combined with the kinase zone.

It is important to note that the spatially sensitive ATP sensing system is also adaptable to the bacterial luciferase, NADH, or NADPH system (14, 16, 17) and to a variety of chemiluminescent systems (4, 6). It is also important to note that, the other 30 plus different bioluminescent systems identified so far in nature have not been studied nearly as well as the firefly and bioluminescent marine bacteria systems (with the possible exception of calcium monitoring based on aequorin and related photoproteins). It has been estimated that there are at least 30 and may indeed be several hundred different, unique, bioluminescent systems involving different luciferases, luciferins and co-factors (1,14). It is conceivable that some fraction of these systems could be employed in the manner disclosed here to be effective biosensors for many of the biochemicals linked to ATP, NADH and NAD(P)H transformations.

The following references are incorporated herein by this reference:

1. Special issue, "Bioluminescence in the Sea," *Naval Research Reviews* 45 (1993) (#2).
2. J. Lee, "Bioluminescence: Biochemistry for Fun and Profit," in D. P. Valenzeno, ed., *Photobiological Techniques*, Plenum, 1991, pp. 297–321.
3. C.-Y. Wang, S. Hitz, J. D. Andrade, and R. J. Stewart, "Specific Immobilization of Firefly Luciferase through a Biotin Carboxyl Carrier Protein Domain",*Anal.Biochem.*, (submitted 1996).
4. I. Bronstein and A. Sparks, ". . . Enzyme Immunoassays With Chemilum . . . ," in R. M. Nakamura, et al., eds., *Immunochemical Assays and Biosensor Technology*, Amer. Soc. Microbiol., 1992. pp. 229–250.
5. F. H. Harold, *The Vital Force: Bioenergetics*, W. H. Freeman, Co., 1986.
6. L. J. Kricka, et al., *Anal. Applic. of Bioluminescence and Chemiluminescence*, Acad. Press., 1989.
7. L. J. Blum, et al., "Design of Luminescence Photobiosensors," *J. Biolum. Chemilum.* 4 (1989) 543–550.
8. P. R. Coulet, "Luciferase-based Sensors," in Proc. Second World Congress on Biosensors, *Biosensors* 92, Elsevier Adv. Tech., pp. 2–9.
9. P. J. Worsfold and A. Nabi, "Bioluminescent Assays . . . ," *Anal. Chim. Acta* 179 (1986) 307.
10. P. Buser and M. Imbert *Vision* (MIT Press, Cambridge, Mass., 1992).
11. P. E. Stanley, B. J. McCarthy, and R. Smither *ATP Luminescence*, (Blackwell Scientific Publications, London 1989).
12. U. Wollenberger, et al., "Biosensor for ADP . . . ," *Anal. Lett.* 20 (1987) 657–668.
13. U. Wollenberger, et al., "Enhancing Biosensor Performance Using Multienzyme Systems, *TIBTech* 11 (1993) 255–262.
14. J. W. Hastings, "Bioluminescence in Bacteria and Dinoflagellates," in *Light Emission by Plants and Bacteria*, Acad. Press, 1986, pp. 363–398.
15. R. F. Zuk, et al., "Enzyme Immunochromatography," *Clin. Chem.* 31 (1985) 1144–1150.
16. S. M. Gautier, et al., "Bioluminescence-Based Fibre-Optic Sensor With Entrapped Co-Reactant . . . ," *Analytica Chimica Acta* 243 (1991) 149–156.
17. A. Nabi and P. J. Worsfold, ". . . Assays . . . Using Immobilized Bacterial Luciferase," *Analytical Leters*, 22 (1989) 1861–1871.
18. M. Dixon and E. C. Webb, *Enzymes*, (Academic Press, New York, 1979).

The invention is further explained by reference to the following illustrative examples:

EXAMPLES

Example I

Figure 14:
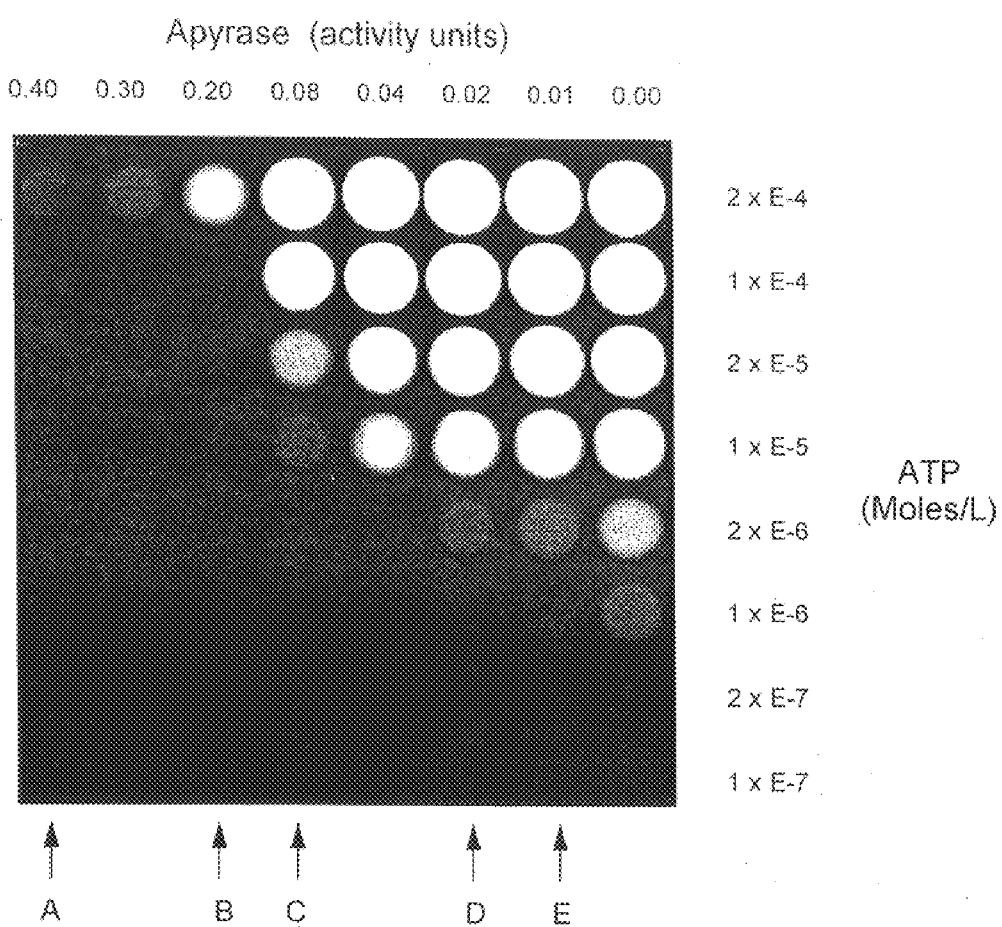
FIG. 14 depicts an eight by eight section of a ninety-six well culture plate and the effect of an apyrase step-concentration gradient on ATP detection threshold as per EXAMPLE I.

FIG. 14 depicts the spatial light distribution for analyte ATP quantification in apyrase step-concentration gradient, another device capable of generating an analyte-specific luminescent signal in a specific spatial position. An eight by eight well section of a ninety-six well MICROTEST tissue culture plate (FALCON 3072) was used to create an ATP assay. The apyrase gradient was formulated as a composite of a logarithmic gradient (0.01, 0.02, 0.04, and 0.08 apyrase activity units) and a linear gradient (0.20, 0.30, and 0.40 apyrase activity units). Each of the eight rows shown in FIG. 14 has the same apyrase gradient and, consequently, this assay is composed of eight identical biosensors. Each of eight different ATP concentrations is applied to one of the eight identical biosensors and the resultant luminescent pattern after five minutes was noted visually in the dark by an observer and then photographed with a cooled, CCD camera (Photometrics Model CH220) with an image integration time of ten seconds. The luminescence pattern was imaged on the CCD array with an F13 macrolens positioned 40 cm above the sample.

The visual detection limit was the lowermost row of FIG. 14, which corresponded to 0.1 micromolar ATP (25 picomoles ATP in 250 μl). The CCD etection limit under these circumstances was 1 micromolar ATP (250 picomoles ATP in 250 μl). It was determined that this particular ATP biosensor could quantitatively indicate ATP over a range of 0.2 millimolar to 1.0 micromolar ATP with the particular CCD detector and 0.2 millimolar to 0.1 micromolar with visual detection in the dark. The actual quantitative determination of ATP was made by looking at the spatial illumination pattern of each of the eight sensors and noting the position of the last visible luminous circle, e.g. positions A, B, C, D and E in FIG. 14 would correspond to ATP analyte concentrations of 0.2 millimolar, 0.1 millimolar, 0.01 millimolar, 2 micromolar, and 1 micromolar ATP, respectively.

After viewing the disclosure herein, various modifications will become apparent to one of skill in the art. For instance, one could formulate different apyrase gradients and concentration ranges to broaden the sensitivity range, narrow the sensitivity range, enhance accuracy, or extend the sensitivity range to lower analyte concentrations. One could also modify the biosensor geometry and optical signal collection to collect more of the luminescent signal thus extending the detection threshold to a lower concentration. One could also place very sensitive photographic film adjacent the biosensor luminescent sources to increase the actual amount of luminescent signal collection, thus extending the detection threshold to lower values, while providing for a permanent record of the test results.

The present invention may be embodied in other specific forms without departing from its spirit or essential characteristics. The described embodiments are to be considered in all respects only as illustrative and not restrictive. The scope of the invention is, therefore, indicated by the appended claims as interpreted in view of the foregoing description. All changes which come within the meaning and range of equivalency of the claims are to be embraced within their scope.

What is claimed is:

1. A method of quantifying a chemical's concentration in a sample comprising:
   placing a quantity of the sample in a device for generating an analyte-specific luminescent signal in a specific spatial position;
   allowing the sample to react with said device for generating an analyte-specific luminescent signal, said analyte-specific luminescent signal being generated by protection of the analyte;
   determining the spatial position of the luminescent signal; and
   comparing the spatial position of the luminescent signal to a reference associated with said device for generating an analyte-specific luminescent signal, said reference being pre-determinedly associated with the chemical's concentration in the sample to be analyzed.

2. The method according to claim 1 wherein the sample is a liquid.

3. The method according to claim 2 further comprising analyzing a ligand of a specific recognition element.

4. The method according to claim 1 wherein the sample is preconcentrated.

5. The method according to claim 4 further comprising analyzing a ligand of a specific recognition element.

6. The method according to claim 1 wherein the spatial position of the luminescent signal is determined with an electronic device.

7. The method according to claim 1 further comprising analyzing a ligand of a specific recognition element.

8. The method according to claim 7 wherein the specific recognition element is an enzyme of established concentration, and the ligand is a substrate capable of reacting with said enzyme.

9. The method according to claim 1 further comprising analyzing a ligand of a specific recognition element.

10. A method of quantifying a chemical's concentration in a sample comprising:
    placing a quantity of the sample in a device for generating an analyte-specific luminescent signal in a specific spatial position;
    allowing the sample to react with said device for generating an analyte-specific luminescent signal, said analyte-specific luminescent signal being generated by a selective consumption of an analyte;
    determining the spatial position of the luminescent signal; and
    comparing the spatial position of the luminescent signal to a reference associated with said device for generating an analyte-specific luminescent signal, said reference being pre-determinedly associated with the chemical's concentration in the sample to be analyzed.

11. The method according to claim 10 wherein the sample is preconcentrated.

12. The method according to claim 11 further comprising analyzing a ligand of a specific recognition element.

13. The method according to claim 10 further comprising analyzing a ligand of a specific recognition element.

14. A method of quantifying a chemical's concentration in a sample comprising:
    placing a quantity of the sample in a device for generating an analyte-specific luminescent signal in a specific spatial position;
    allowing the sample to react with said device for generating an analyte-specific luminescent signal, said analyte-specific luminescent signal being generated by a bioluminescent device;
    determining the spatial position of the luminescent signal; and
    comparing the spatial position of the luminescent signal to a reference associated with said device for generating an analyte-specific luminescent signal, said reference being pre-determinedly associated with the chemical's concentration in the sample to be analyzed.

15. The method according to claim 14 further comprising analyzing a ligand of a specific recognition element.

16. A method of quantifying a chemical's concentration in a solid sample comprising:
    combining the solid sample with a carrier fluid;
    placing a quantity of the solid sample and the carrier fluid in a device for generating an analyte-specific luminescent signal in a specific spatial position;
    allowing the solid sample and the carrier fluid to react with said device for generating an analyte-specific luminescent signal;
    determining the spatial position of the luminescent signal; and
    comparing the spatial position of the luminescent signal to a reference associated with said device for generating an analyte-specific luminescent signal, said reference being pre-determinedly associated with the chemical's concentration in the solid sample to be analyzed.

17. The method according to claim 16 further comprising analyzing a ligand of a specific recognition element.

18. A method of quantifying a chemical's concentration in a sample comprising:
    placing a quantity of the sample in a device for generating an analyte-specific luminescent signal in a specific spatial position;
    allowing the sample to react with said device for generating an analyte-specific luminescent signal;
    determining the spatial position of the luminescent signal; and
    comparing the spatial position of the luminescent signal to a reference associated with said device for generating an analyte-specific luminescent signal, said reference being pre-determinedly associated with the chemical's concentration in the sample to be analyzed wherein the device for generating an analyte-specific luminescent signal includes a bacterial luciferase enzyme specific to the group consisting of NADH and NADPH.

19. The method according to claim 18 further comprising analyzing a ligand of a specific recognition element.

20. A method of quantifying a chemical's concentration in a sample comprising:

placing a quantity of the sample in a device for generating an analyte-specific luminescent signal in a specific spatial position;

allowing the sample to react with said device for generating an analyte-specific luminescent signal, said analyte-specific luminescent signal being generated by production of an analyte;

determining the spatial position of the luminescent signal; and comparing the spatial position of the luminescent signal to a reference associated with said device for generating an analyte-specific luminescent signal, said reference being pre-determinedly associated with the chemical's concentration in the sample to be analyzed, wherein said device for generating an analyte-specific luminescent signal includes a firefly luciferase specific to ATP or processes dependent on ATP.

21. The method according to claim 20 wherein the ligand is of known concentration, and wherein the method further comprises:

analyzing the specific recognition element's concentration or activity.

22. The method according to claim 20 further comprising analyzing a ligand of a specific recognition element.

23. A method of quantifying a chemical's concentration in a sample comprising:

placing a quantity of the sample in a device for generating an analyte-specific luminescent signal in a specific spatial position;

allowing the sample to react with said device for generating an analyte-specific luminescent signal;

determining the spatial position of the luminescent signal; and comparing the spatial position of the luminescent signal to a reference associated with said device for generating an analyte-specific luminescent signal, said reference being pre-determinedly associated with the chemical's concentration in the sample to be analyzed, wherein the device for generating an analyte-specific luminescent signal further includes a dinoflagellate luciferase, bacterial luciferases, genetically engineered luciferases or chemically modified luciferases.

24. The method according to claim 23 further comprising analyzing a ligand of a specific recognition element.

25. A method of quantifying a chemical's concentration in a sample comprising:

placing a quantity of the sample in a device for generating an analyte-specific luminescent signal in a specific spatial position;

allowing the sample to react with said device for generating an analyte-specific luminescent signal, said luminescent signal being generated using a chemiluminescence device;

determining the spatial position of the luminescent signal; and comparing the spatial position of the luminescent signal to a reference associated with said device for generating an analyte-specific luminescent signal, said reference being pre-determinedly associated with the chemical's concentration in the sample to be analyzed.

26. The method according to claim 25 further comprising analyzing a ligand of a specific recognition element.

27. A method of quantifying a chemical's concentration in a sample comprising:

placing a quantity of the sample in a device for generating an analyte-specific luminescent signal in a specific spatial position;

allowing the sample to react with said device for generating an analyte-specific luminescent signal;

determining the spatial position of the luminescent signal; and comparing the spatial position of the luminescent signal to a reference associated with said device for generating an analyte-specific luminescent signal, said reference being pre-determinedly associated with the chemical's concentration in the sample to be analyzed.

28. A method of quantifying a chemical's concentration in a sample comprising:

placing a quantity of the sample in a device for generating an analyte-specific luminescent signal in a specific spatial position;

allowing the sample to react with said device for generating an analyte-specific luminescent signal;

determining the spatial position of the luminescent signal; and comparing the spatial position of the luminescent signal to a reference associated with said device for generating an analyte-specific luminescent signal, said reference being pre-determinedly associated with the chemical's concentration in the sample to be analyzed wherein the device for generating an analyte-specific luminescent signal includes a bacterial luciferase enzyme specific to the group consisting of; processes dependent on NADH and processes dependent on NADPH.

* * * * *